United States Patent [19]
Capiris et al.

[11] Patent Number: 6,051,605
[45] Date of Patent: Apr. 18, 2000

[54] METHOD OF TREATING PSYCHOSIS AND SCHIZOPHRENIA

[75] Inventors: Thomas Capiris, Plymouth; David Thomas Connor, Ann Arbor; Steven Robert Miller, Ann Arbor; Paul Charles Unangst, Ann Arbor; Lawrence David Wise, Ann Arbor, all of Mich.

[73] Assignee: Warner-Lambert Company, Morris Plains, N.J.

[21] Appl. No.: 09/240,949

[22] Filed: Jan. 29, 1999

Related U.S. Application Data

[62] Division of application No. 08/907,681, Aug. 8, 1997, abandoned.

[51] Int. Cl.⁷ ..................................................... A01N 37/38
[52] U.S. Cl. ..................... 514/523; 514/524; 514/525; 514/533; 514/539; 514/561; 514/562; 514/563; 514/564; 514/566; 514/567; 514/616; 514/618; 514/620; 514/622; 514/646; 514/649; 514/651; 514/652; 514/653; 514/654; 514/655
[58] Field of Search ..................................... 514/523, 524, 514/525, 533, 539, 561, 562, 563, 564, 566, 567, 616, 618, 620, 622, 646, 649, 651, 652, 653, 654, 655

[56] References Cited

U.S. PATENT DOCUMENTS

| | | | |
|---|---|---|---|
| 2,547,365 | 4/1951 | Bock et al. | 260/567.6 |
| 2,599,001 | 6/1952 | Kerwin et al. | 260/570.7 |
| 3,154,581 | 10/1964 | Dice | 260/570.7 |
| 3,159,676 | 12/1964 | Spickett et al. | 260/564 |
| 3,192,253 | 6/1965 | Boscott et al. | 260/501 |
| 3,663,712 | 5/1972 | Schmelling et al. | 424/330 |
| 4,010,280 | 3/1977 | Maruyama et al. | 424/316 |

OTHER PUBLICATIONS

Augstein, J. et al., "Some Cardiovascular Effects of a Series of Aryloxyalkylamines," *Journal of Medicinal Chemistry*, May 1965, vol. 8, pp. 356–367.

Smith, L. H. and Tucker, H., "β–Adrenergic Blocking Agents. 17. 1–Phenoxy–3–phenoxyalkylamino–2–propanols and 1–Alkoxyalkylamino–3–phenoxy–2propanols," *Journal of Medicinal Chemistry*, 1977, vol. 20, No. 12, pp. 1653–1656.

J. Augstein, et al., *J Med Chem*, "Some Cardiovascular Effects of a Series of Aryloxyalkylamines," 1965, 8, 356.

L.H. Smith, et al, *J Med Chem*, "β–Adrenergic Blocking Agents. 17. 1–Phenoxy–3–phenoxyalkylamino–2–propanols and 1–Alkoxyalkylamino–3–phenoxy–2–propanols," 1977, 20:12, 1653–1656.

*Primary Examiner*—Frederick Krass
*Attorney, Agent, or Firm*—Linda A. Vag

[57] ABSTRACT

This invention relates to compounds that are antagonists of dopamine D4 receptors, and to methods of treating psychosis and schizophrenia using a compound that is an antagonist of dopamine D4 receptors.

13 Claims, No Drawings

METHOD OF TREATING PSYCHOSIS AND SCHIZOPHRENIA

This application is a divisional of U.S. Ser. No. 08/907,681, filed Aug. 8, 1997 now abandoned.

FIELD OF THE INVENTION

This invention relates to compounds that are antagonists of dopamine D4 receptors and to methods of treating psychosis and schizophrenia using a compound that is an antagonist of dopamine D4 receptors.

BACKGROUND OF THE INVENTION

Dopamine is a neurotransmitter that is found in the brains of animals, including humans, and is essential for proper nerve signal transmission. It is well-known that certain compounds block or inhibit the binding of dopamine to dopamine receptors. Such compounds are called dopamine receptor antagonists. It is also well-known that dopamine receptor antagonists are useful in the treatment of schizophrenia and psychosis.

Recently, it has been discovered that more than one type of dopamine receptor exists, and that dopamine receptor antagonists can preferentially inhibit one type of dopamine receptor over another. Two major families of dopamine receptors have been identified and named the D1 and D2 families. In the D2 family, three distinct receptor subtypes have been identified as D2, D3, and D4.

The distribution and concentration of the subtypes of receptors varies in different regions of the brain. For example, D2 receptors are found in high concentrations in the frontal cortex and limbic region, which are associated with cognitive and emotional function and also in striatal regions which are associated with motor activity.

D2 subtype receptor antagonists have been used to treat psychosis and schizophrenia, but have undesirable extrapyramidal side effects and produce tardive dyskinesia which is thought to be due to their striatal effects. In contrast, D4 receptors are found in highest concentrations in the frontal cortex and limbic regions. Therefore, D4 receptor antagonists can produce antipsychotic efficacy and lack the extra pyromidal side effects and tardive dyskinesias. Moreover, it has been observed that the levels of dopamine D4 receptors are elevated in schizophrenics.

Thus, it would be useful to have compounds that are selective D4 antagonists for the treatment of psychosis and schizophrenia.

U.S. Pat. No. 4,010,280, issued to Sumitomo Chemical Company, discloses phenoxyalkylamine derivatives. However, the compounds exemplified in that patent all have substituents at the ortho position of one of the phenyl rings.

SUMMARY OF THE INVENTION

The present invention provides a method of treating psychosis or schizophrenia, the method comprising administering to a patient suffering therefrom a therapeutically effective amount of a compound having the Formula I

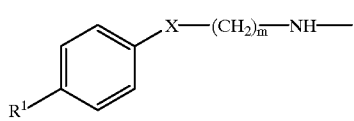

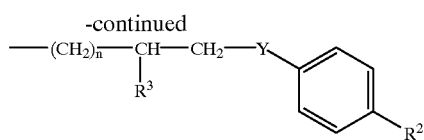

wherein
R$^1$ and R$^2$ are independently hydrogen, hydroxy, C$_1$–C$_6$ alkyl, C$_1$–C$_6$ alkoxy, halogen, nitro, phenyl, cyano, carboxy, carboxyamido, carboxyalkyloxy, C$_1$–C$_6$ alkylamino, or C$_1$–C$_6$ dialkylamino;
R$^3$ is hydrogen, hydroxy, or C$_1$–C$_6$ alkyl;
X and Y are independently CH$_2$, O, S, SO, or SO$_2$;
m and n are independently 1–3;
provided that X and Y are not both CH$_2$, further provided that one of R$^1$ and R$^2$ is not hydrogen, and the pharmaceutically acceptable salts, esters, amides, and prodrugs thereof.

In a preferred embodiment of the invention, R$^3$ is —OH.
In another preferred embodiment, R$^1$ is hydrogen.
In another preferred embodiment, R$^2$ is hydrogen.
In another preferred embodiment, X is CH$_2$ and Y is O.
In another preferred embodiment, X is O and Y is CH$_2$.
In another preferred embodiment, X is O and Y is SO$_2$.
In another preferred embodiment, X is CH$_2$ or O, R$^3$ is OH, and Y is O.
In another preferred embodiment, X is O and Y is O.
In a most preferred embodiment, the compound of Formula I is
Bis-[3-(4-methoxy-phenoxy)-propyl]-amine monohydrochloride;
(3-Phenoxy-propyl)-(2-p-tolyloxy-ethyl)-amine monohydrochloride;
[2-(4-Nitro-phenoxy)-ethyl]-(3-phenoxy-propyl)-amine monohydrochloride;
[2-(4-tert-Butyl-phenoxy)-ethyl]-(3-phenoxy-propyl)-amine monohydrochloride;
[2-(4-Chloro-phenoxy)-ethyl]-(3-phenoxy-propyl)-amine monohydrochloride;
[2-(Biphenyl-4-yloxy)-ethyl]-(3-phenoxy-propyl)-amine monohydrochloride;
(2-p-Tolyloxy-ethyl)-(3-p-tolyloxy-propyl)-amine monohydrochloride;
[3-(4-Bromo-phenoxy)-propyl]-(2-p-tolyloxy-ethyl)-amine monohydrochloride;
[2-(4-Chloro-phenoxy)-ethyl]-(3-p-tolyloxy-propyl)-amine monohydrochloride;
(2-Phenoxy-ethyl)-(3-p-tolyloxy-propyl)-amine monohydrochloride;
[3-(4-Bromo-phenoxy)-propyl]-[2-(4-chloro-phenoxy)-ethyl]-amine monohydrochloride;
[3-(4-Fluoro-phenoxy)-propyl]-(2-phenoxy-ethyl)-amine monohydrochloride;
Bis-[3-(4-bromo-phenoxy)-propyl]-amine monohydrochloride;
Bis-(3-p-tolyloxy-propyl)-amine monohydrochloride;
[3-(4-Fluoro-phenoxy)-propyl]-(2-p-tolyloxy-ethyl)-amine monohydrochloride;
(3-Phenoxy-propyl)-(2-p-tolylsulfanyl-ethyl)-amine monohydrochloride;
[2-(4-Chloro-phenylsulfanyl)-ethyl]-(3-phenoxy-propyl)-amine monohydrochloride;
[2-(4-Chloro-phenoxy)-ethyl]-(3-phenylsulfanyl-propyl)-amine monohydrochloride;
(3-Phenylsulfanyl-propyl)-(2-p-tolyloxy-ethyl)-amine monohydrochloride;
[2-(4-Chloro-phenoxy)-ethyl]-[3-(4-fluoro-phenoxy)-propyl]-amine monohydrochloride;

(3-Phenoxy-propyl)-(3-p-tolyl-propyl)-amine monohydrochloride;
4-[2-(3-Phenoxy-propylamino)-ethoxy]-benzoic acid methyl ester;
4-[2-(3-Phenoxy-propylamino)-ethoxy]-benzonitrile;
(2-Phenoxy-ethyl)-(2-p-tolyloxy-ethyl)-amine monohydrochloride;
Bis-(2-p-tolyloxy-ethyl)-amine monohydrochloride;
[2-(4-Methoxy-phenoxy)-ethyl]-(3-phenoxy-propyl)-amine monohydrochloride;
4-[2-(3-Phenoxy-propylamino)-ethoxy]-phenol monohydrobromide;
4-[2-(3-Phenoxy-propylamino)-ethoxy]-benzoic acid monohydrochloride;
1-Phenoxy-3-(2-p-tolyloxy-ethylamino)-propan-2-ol;
1-[2-(4-Chloro-phenoxy)-ethylamino]-3-phenoxy-propan-2-ol;
[3-(4-Bromo-phenoxy)-propyl]-(2-phenoxy-ethyl)-amine monohydrochloride; and
[2-(4-Ethoxy-phenoxy)-ethyl]-(3-phenoxy-propyl)-amine monohydrochloride.

Also provided by the present invention are the following compounds:
Bis-[3-(4-methoxy-phenoxy)-propyl]-amine monohydrochloride;
(3-Phenoxy-propyl)-(2-p-tolyloxy-ethyl)-amine monohydrochloride;
[2-(4-Nitro-phenoxy)-ethyl]-(3-phenoxy-propyl)-amine monohydrochloride;
[2-(4-tert-Butyl-phenoxy)-ethyl]-(3-phenoxy-propyl)-amine monohydrochloride;
[2-(4-Chloro-phenoxy)-ethyl]-(3-phenoxy-propyl)-amine monohydrochloride;
[2-(Biphenyl-4-yloxy)-ethyl]-(3-phenoxy-propyl)-amine monohydrochloride;
(2-p-Tolyloxy-ethyl)-(3-p-tolyloxy-propyl)-amine monohydrochloride;
[3-(4-Bromo-phenoxy)-propyl]-(2-p-tolyloxy-ethyl)-amine monohydrochloride;
[2-(4-Chloro-phenoxy)-ethyl]-(3-p-tolyloxy-propyl)-amine monohydrochloride;
(2-Phenoxy-ethyl)-(3-p-tolyloxy-propyl)-amine monohydrochloride;
[3-(4-Bromo-phenoxy)-propyl]-[2-(4-chloro-phenoxy)-ethyl]-amine monohydrochloride;
[3-(4-Fluoro-phenoxy)-propyl]-(2-phenoxy-ethyl)-amine monohydrochloride;
Bis-[3-(4-bromo-phenoxy)-propyl]-amine monohydrochloride;
Bis-(3-p-tolyloxy-propyl)-amine monohydrochloride;
[3-(4-Fluoro-phenoxy)-propyl]-(2-p-tolyloxy-ethyl)-amine monohydrochloride;
(3-Phenoxy-propyl)-(2-p-tolylsulfanyl-ethyl)-amine monohydrochloride;
[2-(4-Chloro-phenylsulfanyl)-ethyl]-(3-phenoxy-propyl)-amine monohydrochloride;
[2-(4-Chloro-phenoxy)-ethyl]-(3-phenylsulfanyl-propyl)-amine;
(3-Phenylsulfanyl-propyl)-(2-p-tolyloxy-ethyl)-amine monohydrochloride;
[2-(4-Chloro-phenoxy)-ethyl]-[3-(4-fluoro-phenoxy)-propyl]-amine monohydrochloride;
(3-Phenoxy-propyl)-(3-p-tolyl-propyl)-amine monohydrochloride;
4-[2-(3-Phenoxy-propylamino)-ethoxy]-benzoic acid methyl ester;
4-[2-(3-Phenoxy-propylamino)-ethoxy]-benzonitrile;
(2-Phenoxy-ethyl)-(2-p-tolyloxy-ethyl)-amine monohydrochloride;
Bis-(2-p-tolyloxy-ethyl)-amine monohydrochloride;
[2-(4-Methoxy-phenoxy)-ethyl]-(3-phenoxy-propyl)-amine monohydrochloride;
4-[2-(3-Phenoxy-propylamino)-ethoxy]-phenol monohydrobromide;
4-[2-(3-Phenoxy-propylamino)-ethoxy]-benzoic acid monohydrochloride; and
[2-(4-Ethoxy-phenoxy)-ethyl]-(3-phenoxy-propyl)-amine monohydrochloride.

DETAILED DESCRIPTION OF THE INVENTION

This invention provides a method of treating psychosis or schizophrenia, the method comprising administering to a patient suffering therefrom a therapeutically effective amount of a compound having the Formula I

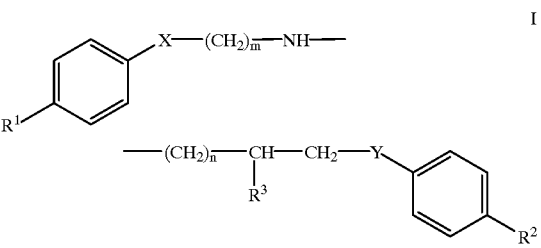

wherein
$R^1$ and $R^2$ are independently hydrogen, hydroxy, $C_1$–$C_6$ alkyl, $C_1$–$C_6$ alkoxy, halogen, nitro, phenyl, cyano, carboxy, carboxyamido, carboxyalkyloxy; $C_1$–$C_6$ alkylamino or $C_1$–$C_6$ dialkylamino;
$R^3$ is hydrogen, hydroxy, or $C_1$–$C_6$ alkyl;
X and Y are independently $CH_2$, O, S, SO, or $SO_2$;
m and n are independently 1–3;
provided that X and Y are not both $CH_2$, further provided that one of $R^1$ and $R^2$ is not hydrogen, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "carboxy" means a carboxylic acid functional group, i.e., —$CO_2H$.

The term "carboxyalkyloxy" means an alkyl ester of a carboxylic acid functional group, i.e., —$CO_2$alkyl. A preferred carboxyalkyloxy group is carboxymethoxy.

The term "carboxyamide" means a —$CONH_2$ group. It is noted that the two hydrogens on the nitrogen atom may be substituted with substituents that are well-known to those skilled in the art, such as alkyl groups.

The symbol "—" means a bond.

The term "patient" means humans.

A "therapeutically effective amount" is an amount of a compound of the present invention that when administered to a patient ameliorates a symptom of psychosis or schizophrenia. A therapeutically effective amount of a compound of the present invention can be easily determined by one skilled in the art by administering a quantity of a compound to a patient and observing the result. In addition, those skilled in the art are familiar with identifying patients having psychosis and schizophrenia and are readily able to identify patients who suffer from psychosis and schizophrenia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient alone or as part of a composition that contains other components such as excipients, diluents, and carriers, all of which are well-known in the art.

The compositions can be administered to humans and animals either orally, rectally, parenterally (intravenously, intramuscularly, or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferred. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof, including racemic mixtures, form part of this invention.

The following examples are intended to illustrate particular embodiments of the invention and are not intended to limit the scope of the disclosure or the claims in any manner.

EXAMPLES

The compounds of the present invention are prepared by the following methods, as illustrated in Schemes I–II.

Substituted amines (2) and substituted halides (3) are combined in a solvent such as benzene, toluene, xylene, ethanol, or N,N-dimethylformamide and heated at 70° C. to 140° C. for 8 to 48 hours. An additional molar equivalent of the amine may be added in order to trap the acid liberated in the reaction, or an additional base such as sodium carbonate or potassium carbonate may be included for this purpose. As starting materials, amines (2) are known or are readily prepared by known methods, such as Augstein J., et al., *J. Med. Chem.*, 8:356 (1965), and Soffer L. M., et al., *J. Amer. Chem. Soc.*, 76:3580 (1954). Similarly, halides (3) are known or are readily prepared by known methods, such as Reinholz E., et al., *Synthesis*, 1069 (1990), and Bakuzis P., et al., *J. Org. Chem.*, 41:2769 (1976).

Substituted carboxylic acids (4) may be converted to activated intermediates with isobutyl chloroformate, oxalyl chloride, thionyl chloride, or 1,1'-carbonyldiimidazole and these intermediates reacted with amines (2) in order to form amides (5). The reaction is carried out at 0° C. to 25° C. in a solvent such as tetrahydrofuran, toluene, or dichloromethane for 1 to 24 hours in the presence of a base such as triethylamine or N,N-diisopropylethylamine.

The intermediate amides (5) are then reduced to the compounds of the present invention by treatment with metal hydride complexes, such as lithium aluminum hydride, lithium aluminum hydride-aluminum chloride, or sodium borohydride-aluminum chloride. The reaction may be performed in ether, tetrahydrofuran, ethanol, or dioxane at 0° C. to 80° C. for 1 to 24 hours. Carboxylic acids (4) are known or a methods, such as ed by known methods, such as Collins M. J., et al., *Aust. J. Chem.*, 43:1547 (1990).

Compounds of the present invention containing a hydroxyl group in a position beta to the amine (7) are conveniently prepared by the well-known method (Crowther A. F., et al., *J. Med. Chem.*, 12:638 (1969)) of condensing an amine (2) with a substituted epoxide (6).

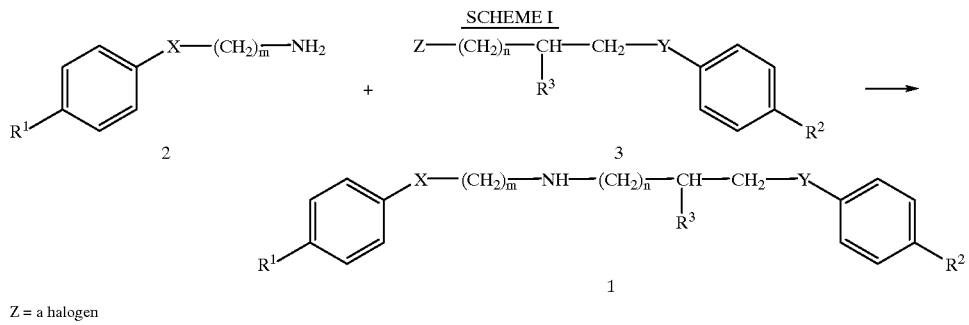

SCHEME I

SCHEME II

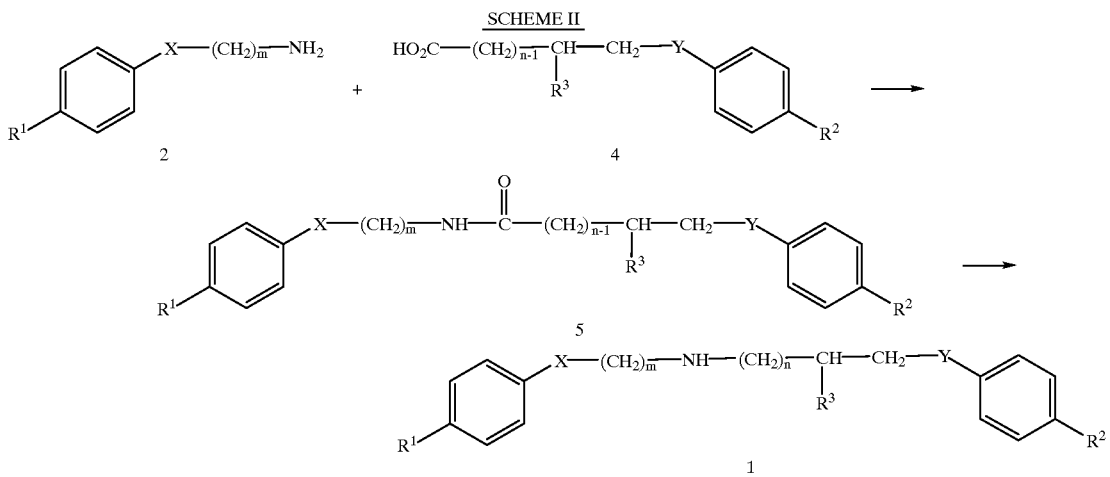

SCHEME III

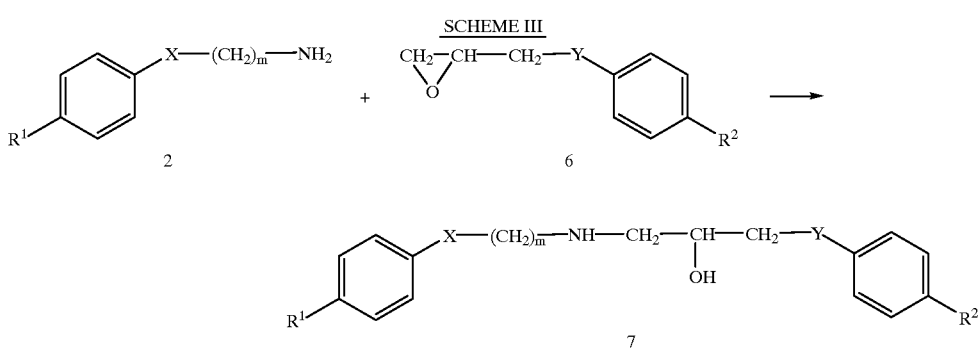

Example 1
(3-Phenoxy-propyl)-(3-phenyl-propyl)-amine hydrochloride

A mixture of (3-bromopropoxy)benzene (1.6 mL, 2.2 g, 10.2 mmol) and benzenepropanamine (2.8 mL, 2.7 g, 19.7 mmol) in 20 mL of toluene is stirred at reflux for 18 hours. The mixture is cooled, and the precipitated benzenepropanamine hydrobromide is filtered and washed with toluene. The combined filtrates are washed with brine, dried (anhydrous sodium sulfate), and treated with hydrogen chloride gas. The precipitated solid is filtered, washed with ethyl ether, and recrystallized from ethanol and tert-butyl methyl ether to yield 0.90 g (30%) of product, mp 188–191° C.

Similarly prepared are:
(a) Bis-(3-phenoxy-propyl)-amine hydrochloride, mp 144–147° C.;
(b) [2-(2-Chloro-phenoxy)-ethyl]-(3-phenoxy-propyl)-amine amine hydrochloride, mp 135–137° C.;
(c) [2-(2-Ethoxy-phenoxy)-ethyl]-[3-(3-methoxy-phenoxy)-propyl]-amine hydrochloride, mp 59–61° C.;
(d) [2-(2,3-Dichloro-phenoxy)-ethyl]-(3-phenoxy-propyl)-amine hydrochloride, mp 173–174° C.;
(e) [2-(3-Bromo-phenoxy-ethyl]-(3-phenoxy-propyl)-amine hydrochloride, mp 187–189° C.;
(f) 3-[2-(3-Phenoxy-propylamino)-ethoxy]-benzonitrile hydrochloride, mp 172–174° C.;
(g) (3-Phenoxy-propyl)-(2-m-tolyloxy-ethyl)-amine hydrochloride, mp 184–187° C.;
(h) [2-(3-Nitro-phenoxy)-ethyl]-(3-phenoxy-propyl)-amine hydrochloride, mp 175–177° C.;
(i) [2-(3-Chloro-phenoxy)-ethyl]-(3-phenoxy-propyl)-amine hydrochloride, mp 185–187° C.;
(j) 3-[2-(3-Phenoxy-propylamino)-ethoxy]-benzoic acid methyl ester hydrochloride, mp 196–198° C.;
(k) [2-(Biphenyl-3-yloxy)-ethyl]-(3-phenoxy-propyl)-amine hydrochloride, mp 201–204° C.;
(l) 2-[2-(3-Phenoxy-propylamino)-ethoxy]-benzonitrile hydrochloride, mp 151–153° C.;
(m) [2-(3-Ethoxy-phenoxy)-ethyl]-(3-phenoxy-propyl)-amine hydrochloride, mp 181–183° C.;
(n) [3-(3-Methoxy-phenoxy)-propyl]-(3-phenyl-propyl)-amine hydrochloride, mp 145–147° C.;
(o) [2-(3-Chloro-4-methyl-phenoxy)-ethyl]-(3-phenoxy-propyl)-amine hydrochloride, mp 212–214° C.;
(p) [2-(3,4-Dimethyl-phenoxy)-ethyl]-(3-phenoxy-propyl)-amine hydrochloride, mp 193–195° C.;
(q) Bis[3-(4-methoxy-phenoxy)-propyl]-amine hydrochloride, mp 218–221° C.; and
(r) [3-(4-Chloro-phenoxy)-propyl]-[2-(3,4,5-trimethoxy-phenoxy)-ethyl]-amine hydrochloride, mp 120–123° C.

Example 2
(3-Phenoxy-propyl)-(2-p-tolyloxy-ethyl)-amine hydrochloride

A solution of 3-phenoxy-1-propanamine (3.0 g, 20 mmol) in 10 mL of benzene is heated to reflux and treated over 15 minutes with a solution of 1-(2-bromoethoxy)-4-methylbenzene (2.2 g, 10 mmol) in 10 mL of benzene. The mixture is stirred at reflux for 18 hours, then cooled, and the precipitated 3-phenoxy-1-propanamine hydrobromide is filtered. A solution of 4.0 M hydrochloric acid in dioxane (3.0 mL) is added to the filtrate, and the mixture is stirred for 15 minutes. The precipitated salt is filtered and recrystallized from ethanol to yield 1.8 g (56%) of product, mp 210–215° C.

Similarly prepared are:
(a) [2-(4-Nitro-phenoxy)-ethyl]-(3-phenoxy-propyl)-amine hydrochloride, mp 160–162° C.;
(b) [2-(4-tert-Butyl-phenoxy)-ethyl]-(3-phenoxy-propyl)-amine hydrochloride, mp 194–196° C.;
(c) [2-(4-Ethoxy-phenoxy)-ethyl]-(3-phenoxy-propyl)-amine hydrochloride, mp 214–216° C.;
(d) [2-(4-Chloro-phenoxy)-ethyl]-(3-phenoxy-propyl)-amine hydrochloride, mp 205–206° C.; and
(e) [2-(Biphenyl-4-yloxy)-ethyl]-(3-phenoxy-propyl)-amine hydrochloride, mp 246–248° C.

Example 3

(2-p-Tolyloxy-ethyl)-(3-p-tolyloxy-propyl)-amine hydrochloride

A mixture of 2-(4-methylphenoxy)ethanamine (1.5 g, 10 mmol), 1-(3-bromopropoxy)-4-methylbenzene (2.3 g, 10 mmol), and anhydrous sodium carbonate (0.75 g, 7.1 mmol) in 15 mL of N,N-dimethylformamide is heated in an oil bath at 90° C. for 18 hours. The cooled reaction mixture is added to 300 mL of water and extracted with toluene. The combined organic layers are washed with brine, dried (anhydrous sodium sulfate), and evaporated. The residue is dissolved in 100 mL of ethyl ether, and the solution is treated with hydrogen chloride gas. The precipitated solid is filtered, washed with ethyl ether, and recrystallized from acetonitrile and methanol to yield 1.1 g (30%) of product, mp 230–232° C.

Similarly prepared are:
(a) [2-(Biphenyl-2-yloxy)-ethyl]-(3-phenoxy-propyl)-amine hydrochloride, mp 69–72° C.;
(b) [3-(4-Bromo-phenoxy)-propyl]-(2-p-tolyloxy-ethyl)-amine hydrochloride, mp 240–243° C.
(c) [3-(3-Methoxy-phenoxy)-propyl]-(2-p-tolyloxy-ethyl)-amine hydrochloride, mp 172–175° C.;
(d) [3-(3,4-Dimethyl-phenoxy)-propyl]-(2-p-tolyloxy-ethyl)-amine hydrochloride, mp 203–205° C.;
(e) [2-(4-Chloro-phenoxy)-ethyl]-(3-p-tolyloxy-propyl)-amine hydrochloride, mp 227–230° C.;
(f) (2-Phenoxy-ethyl)-(3-p-tolyloxy-propyl)-amine hydrochloride, mp 209–211° C.; and
(g) [3-(4-Bromo-phenoxy)-propyl]-[2-(4-chloro-phenoxy)-ethyl]-amine hydrochloride, mp 220–223° C.

Example 4

[3-(4-Fluoro-phenoxy)-propyl]-(2-phenoxy-ethyl)-amine hydrochloride

A mixture of 2-phenoxyethanamine (0.70 g, 5.1 mmol), 1-(3-bromopropoxy)-4-fluorobenzene (1.2 g, 5.1 mmol), and potassium carbonate (0.71 g, 5.1 mmol) in 15 mL of N,N-dimethylformamide is heated in an oil bath at 90° C. for 18 hours. The cooled mixture is filtered, and the filtrate is evaporated. The residue is dissolved in ethyl ether, and the solution is treated with hydrogen chloride gas. The precipitated solid is filtered, washed with ethyl ether, and recrystallized from ethanol to yield 0.54 g (33%) of product, mp 189–191° C.

Similarly prepared are:
(a) Bis-[3-(4-bromo-phenoxy)-propyl]-amine hydrochloride, mp 247–248° C.;
(b) Bis(3-p-tolyloxy-propyl)-amine hydrochloride, mp 245–247° C.;
(c) [3-(4-Fluoro-phenoxy)-propyl]-(2-p-tolyloxy-ethyl)-amine hydrochloride, mp 227–228° C.;
(d) (3-Phenoxy-propyl)-(2-p-tolylsulfanyl-ethyl)-amine hydrochloride, mp 155–158° C.;
(e) [2-(4-Chloro-phenylsulfanyl)-ethyl]-(3-phenoxy-propyl)-amine hydrochloride, mp 165–167° C.;
(f) [2-(4-Chloro-phenoxy)-ethyl]-(3-phenylsulfanyl-propyl)-amine hydrochloride, mp 191–194° C.;
(g) (3-Phenylsulfanyl-propyl)-(2-p-tolyloxy-ethyl)-amine hydrochloride, mp 195–198° C.; and
(h) [2-(4-Chloro-phenoxy)-ethyl]-[3-(4-fluoro-phenoxy)-propyl]-amine hydrochloride, mp 194–195° C.

Example 5

(3-Phenoxy-propyl)-(3-p-tolyl-propyl)-amine hydrochloride

N-(3-Phenoxy-propyl)-3-p-tolyl-propionamide
A solution of 4-methylbenzenepropanoic acid (2.0 g, 12.2 mmol) and triethylamine (4.3 mL, 3.1 g, 30.9 mmol) in 80 mL of tetrahydrofuran is cooled in ice and treated dropwise with isobutyl chloroformate (1.7 mL, 1.8 g, 13.1 mmol). The mixture is stirred for 1 hour, and a solution of 3-phenoxy-1-propanamine (1.9 g, 12.6 mmol) in 10 mL of tetrahydrofuran is added slowly. The mixture is stirred at room temperature for 18 hours, then added to 400 mL of brine. The mixture is acidified with 4.0 N hydrochloric acid and extracted with ethyl acetate. The combined organic layers are washed with brine, dried (anhydrous sodium sulfate), and evaporated. Recrystallization of the residue gives 2.2 g (61%) of the amide intermediate product, mp 101–102° C.

A solution of the above amide intermediate (1.0 g, 3.4 mmol) in 15 mL of tetrahydrofuran is added dropwise to a solution of 1.0 M lithium aluminum hydride (8.0 mL, 8.0 mmol) in 15 mL of tetrahydrofuran. The mixture is stirred at reflux for 3 hours, then cooled in ice while 10 mL of water is added dropwise. Toluene (30 mL) is added to the mixture, and the inorganic solids are filtered and washed with water and toluene. The organic layer is separated from the combined filtrates and the aqueous layer is extracted with additional toluene. The combined organic layers are washed with brine, dried (anhydrous sodium sulfate), and evaporated. The residue is dissolved in 100 mL of ethyl ether, and the solution is treated with hydrogen chloride gas. The precipitated solid is filtered, washed with ethyl ether, and recrystallized from acetonitrile to yield 0.60 g (56%) of amine hydrochloride product, mp 214–217° C.

Similarly prepared are:
(a) [2-(2-Ethoxy-phenoxy)-ethyl]-(4-phenyl-butyl)-amine hydrochloride, mp 97–99° C.;
(b) (2-Phenoxy-ethyl)-(3-phenoxy-propyl)-amine hydrochloride, mp 199–201° C.;
(c) [2-(2-Methoxy-phenoxy)-ethyl]-(1-methyl-2-phenoxy-ethyl)-amine, bp 135–139° C. (0.05 mm); and
(d) [3-(3-Methoxy-phenoxy)-propyl]-(3-p-tolyl-propyl)-amine hydrochloride, mp 168–170° C.

Example 6

[2-(3,4-Dichloro-phenoxy)-ethyl]-(3-phenoxy-propyl)-amine hydrochloride

A mixture of 4-(2-bromoethoxy)-1,2-dichlorobenzene (2.0 g, 7.4 mmol) and 3-phenoxy-1-propanamine (2.3 g, 15.2 mmol) in 125 mL of benzene is heated at reflux for 33 hours. The precipitated 3-phenoxy-1-propanamine hydrobromide is filtered, and the filtrate is passed over a column of silica gel. The column is eluted with dichloromethane followed by ethyl acetate. The product fraction is evaporated, and the residue is dissolved in ethyl ether. A solution (2.0 mL) of 4.0 M hydrogen chloride in dioxane is added, and the precipitated salt is filtered and washed with ethyl ether to give 0.61 g (22%) of product, mp 187–189° C.

Similarly prepared are:
(a) 4-[2-(3-Phenoxy-propylamino)-ethoxy]-benzoic acid methyl ester, mp 57–59° C.;
(b) 4-[2-(3-Phenoxy-propylamino)-ethoxy]-benzonitrile, mp 76–77° C.;
(c) 1-[2-(3,4-Dichloro-phenoxy)-ethylamino]-3-phenoxy-propan-2-ol, mp 126–128° C.;
(d) (2-Phenoxy-ethyl)-(2-p-tolyloxy-ethyl)-amine hydrochloride, mp 200–201° C.;
(e) Bis-(2-p-tolyloxy-ethyl)-amine hydrochloride, mp 225–230° C.;
(f) (2-p-Tolyloxy-ethyl)-(3-o-tolyloxy-propyl)-amine hydrochloride, mp 197–199° C.; and
(g) (2-p-Tolyloxy-ethyl)-(3-m-tolyloxy-propyl)-amine hydrochloride, mp 203–204° C.

Example 7

2-[2-(3-Phenoxy-propylamino)-ethoxyl]-benzamide hydrochloride

A mixture of 2-(2-bromoethoxy)benzamide (2.5 g, 10 mmol), 3-phenoxy-1-propanamine (1.5 g, 10 mmol), and potassium carbonate (1.4 g, 10 mmol) in 20 mL of ethanol is stirred at reflux for 18 hours. The cooled solution is filtered, and the filtrate is treated with hydrogen chloride gas. The precipitated solid is filtered, washed with ethyl ether, and recrystallized from acetonitrile to give 1.0 g (29%) of product, mp 119–121° C.

Similarly prepared is:
(a) [2-(2-Nitro-phenoxy)-ethyl]-(3-phenoxy)-propyl)-amine hydrochloride, mp 148–150° C.

Example 8

1-(3-Phenoxy-propylamino)-3-o-tolyloxy-propan-2-ol

A solution of 3-phenoxy-1-propanamine (130 g, 860 mmol) in 375 mL of 95% ethanol is treated in portions with [(2-methylphenoxy)methyl]oxirane (47.5 g, 289 mmol). The reaction mixture is allowed to stand at room temperature for 20 hours, then heated on the steam bath for 1 hour. The solvent and excess amine starting material are removed by evaporation under high vacuum. Recrystallization of the residue from benzene gives 51 g (54%) of product, mp 70–72° C.

Similarly prepared is:
(a) 1-(2-Chloro-phenoxy)-3-(3-phenyl-propylamino)-propan-2-ol, mp 73–74° C.

Example 9

[2-(3-Methoxy-phenoxy)-ethyl]-(3-phenoxy-propyl)-amine hydrochloride

A solution of 3-phenoxy-1-propanamine (45.4 g, 300 mmol) in 200 mL of benzene is heated to reflux and treated slowly with a solution of 1-(2-bromoethoxy)-3-methoxybenzene (34.7 g, 150 mmol) in 100 mL of benzene. The mixture is stirred at reflux for 44 hours, cooled, and the precipitated 3-phenoxy-1-propanamine hydrobromide is filtered. The filtrate is treated with hydrogen chloride gas, and the precipitated salt is filtered and recrystallized from ethanol to give 14.9 g of initial product. The salt is partitioned between sodium hydroxide solution and ethyl ether. The ether layer is dried (anhydrous magnesium sulfate) and evaporated. The residue is distilled under vacuum, and the product fraction is dissolved in ethyl ether. The solution is treated with hydrogen chloride gas. The precipitated solid is filtered and washed with ethyl ether to yield 12.6 g (25%) of product, mp 170–172° C.

Similarly prepared are:
(a) [2-(2-Bromo-phenoxy)-ethyl]-(3-phenoxy-propyl)-amine hydrochloride, mp 134–135° C.;
(b) (3-Phenoxy-propyl)-(2-o-tolyloxy-ethyl)-amine hydrochloride, mp 137–139° C.;
(c) [2-(2-Ethoxy-phenoxy)-ethyl]-[3-(4-methoxy-phenoxy)-propyl]-amine hydrochloride, mp 51–53° C.;
(d) [2-(4-Methoxy-phenoxy)-ethyl]-(3-phenoxy-propyl)-amine hydrochloride, mp 204–206° C.;
(e) [3-(2,3-Dichloro-phenoxy)-propyl]-[2-(2-ethoxy-phenoxy-ethyl]-amine hydrochloride, mp 129–131° C.;
(f) [2-(2-Ethoxy-phenoxy)-ethyl]-[3-(2-ethoxy-phenoxy)-propyl]-amine hydrochloride, mp 74–77° C.; and
(g) (3-Phenoxy-propyl)-[2-(2-propoxy-phenoxy)-ethyl]-amine hydrochloride, mp 129–131° C.

Example 10

1-(2-Phenoxy-ethylamino)-3-m-tolyloxy-propan-2-ol

A mixture of 1-chloro-3-(3-methylphenoxy)-2-propanol (10.0 g, 50 mmol) and 2-phenoxyethanamine (13.7 g, 100 mmol) is heated on the steam bath for 14 hours. The reaction mixture is cooled and treated with a small amount of ethyl acetate. The precipitated 2-phenoxyethanamine hydrochloride is filtered and washed with ethyl acetate. The combined filtrates are washed with brine, dried (anhydrous magnesium sulfate), and evaporated. The residue is treated with a small amount of isopropyl ether. The precipitated solid is filtered to give 6.4 g (42%) of product, mp 70–72° C.

Similarly prepared is:
(a) 1-[2-(3,4-Dichloro-phenyl)-ethylamino]-3-m-tolyloxy-propan-2-ol, mp 81–82° C.

Example 11

4-[2-(3-Phenoxy-propylamino)-ethoxy]-phenol hydrobromide

A solution of 3-phenoxy-1-propanamine (24.2 g, 160 mmol) in 100 mL of 2-propanol is heated to reflux and treated slowly with a solution of 4-(2-bromoethoxy)phenol (17.4 g, 80 mmol) in 150 mL of 2-propanol. The mixture is heated at reflux for 4 days, then cooled and partitioned between ethyl ether and aqueous sodium bicarbonate solution. The organic layer is evaporated and the residue recrystallized from ethanol to give 6.0 g (20%) of product, mp 204–205° C.

Example 12

3-[3-(3-Phenyl-propylamino)-propoxy]-phenol hydrochloride

3-[3-(Phenylmethoxy)phenoxy]-1-propanamine

A mixture of 3-[m-(benzyloxy)phenoxy]-propionitrile (203 g, 0.80 mol) in 2-propanol is hydrogenated over Raney nickel catalyst (50 g). The catalyst is filtered, and the filtrate is evaporated. Distillation of the residue under high vacuum gives 143 g (69%) of product, bp 190° C. (0.15 mm).

[3-(3-Benzyloxy-phenoxy)-propyl]-(3-phenyl-propyl)-amine hydrochloride

A mixture of the above amine (25.8 g, 100 mmol) and (3-chloropropyl)benzene (8.0 g, 52 mmol) in 250 mL of xylene is heated at reflux for 72 hours. The mixture is cooled, and the precipitated amine hydrochloride is filtered.

The filtrate is evaporated, and the residue is dissolved in 2-propanol and treated with hydrogen chloride gas. The precipitated salt is filtered and recrystallized from 2-propanol and ethyl ether to yield 6.0 g (28%) of product, mp 177–178° C.

A mixture of the above amine salt (5.0 g, 12 mmol) in methanol is hydrogenated over 20% palladium on carbon catalyst (0.50 g). The catalyst is filtered, and the filtrate is evaporated. The residue is recrystallized from ethanol and ethyl ether to give 3.5 g (90%) of product, mp 131–132° C.

Example 13

(2-Benzenesulfonyl-ethyl)-[2-(2-ethoxy-phenoxy)-ethyl]-amine hydrochloride

A mixture of 2-(2-ethoxyphenoxy)ethanamine (36.2 g, 200 mmol) and [(2-phenoxyethyl)sulfonyl]-benzene (52.5 g, 200 mmol) in 500 mL of tetrahydrofuran is treated in portions with 50% sodium hydride in mineral oil suspension (9.7 g, 202 mmol). The mixture is stirred at room temperature for 1 hour and then evaporated. The residue is partitioned between ethyl ether and brine. The ether layer is dried (anhydrous magnesium sulfate) and treated with hydrogen chloride gas. The precipitated solid is filtered and recrystallized from ethanol to give 49.6 g (64%) of product, mp 146–152° C.

Example 14

(3-Benzenesulfonyl-propyl)-[2-(2-ethoxy-phenoxy)-ethyl]-amine oxalate

A mixture of [(3-bromopropyl)sulfonyl]benzene (26.3 g, 100 mmol), 2-(2-ethoxyphenoxy)ethanamine (18.1 g, 100 mmol), and potassium carbonate (55.3 g, 400 mmol) in 200 mL of methyl ethyl ketone is heated at reflux for 18 hours. The reaction mixture is cooled, filtered, and the filtrate is evaporated. The residue is dissolved in warm 2-propanol and treated with oxalic acid (9.3 g, 101 mmol). The precipitated salt is filtered and recrystallized from 2-propanol to yield 3.2 g (7%) of product, mp 184–188° C.

Example 15

4-[2-(3-Phenoxy-propylamino)-ethoxy]-benzoic acid hydrochloride

A mixture of 4-[2-(3-phenoxy-propylamino)-ethoxy]-benzoic acid methyl ester (0.34 g, 1.0 mmol) in 10 mL of methanol and 5.0 mL of 2.0 N aqueous sodium hydroxide is heated on the steam bath for 20 minutes. The reaction mixture is diluted with water, and the methanol solvent is evaporated. The residue is acidified with acetic acid and partitioned between dichloromethane and water. The precipitate that forms is filtered and recrystallized from ethanol. The solid is dissolved warm in 30% aqueous ethanol and treated with 0.5 mL of 4.0 M hydrogen chloride in dioxane. The precipitated solid is filtered to give 0.085 g (24%) of product, mp 270–280° C.

The following compounds were also found to be dopamine $D_4$ antagonists:

16a 1-(3-Phenyl-propylamino)-3-o-tolyloxy-propan-2-ol;
16b 1-(3-Phenyl-propylamino)-3-m-tolyloxy-propan-2-ol;
16c [2-(2-Ethoxy-phenoxy)-ethyl]-(3-phenoxy-propyl)-amine hydrochloride;
16d [2-(2-Ethoxy-phenoxy)-ethyl]-(4-phenoxy-butyl)-amine hydrochloride;
16e [2-(2-Methoxy-phenoxy)-ethyl]-(3-phenoxy-propyl)-amine hydrochloride;
16f 4-[2-(2-Hydroxy-3-o-tolyloxy-propylamino)-ethoxy]-benzamide hydrochloride;
16g 1-Phenoxy-3-(2-p-tolyloxy-ethylamino)-propan-2-ol;
16h 1-[2-(4-Chloro-phenoxy)-ethylamino]-3-phenoxy-propan-2-ol;
16i [3-(4-Bromo-phenoxy)-propyl]-(2-phenoxy-ethyl)-amine hydrochloride; and
16j (3-Phenyl-propyl)-(3-phenylsulfanyl-propyl)-amine hydrochloride.

BIOLOGICAL METHODS

Cell Lines Expressing Dopamine Receptor Isoforms

A cell line expressing human dopamine D2 (Long form) receptors was purchased from Oregon Health Sciences University, Portland, Or. The D2 receptor cDNA was subcloned into an expression vector, pRc/CMV. The plasmids were transfected by electroporation into CHO K1 cells. A single stable transfectant, resistant to the antibiotic G418, was isolated and selected for use in the binding studies. For D4 binding, CHO K1 cells stably transfected to express the human recombinant dopamine D4.2 receptor subtype, as described by Shih, et al., "The expression and functional characterization of human dopamine D4.2 receptor in CHO K1 cells," *Soc. Neurosci.*, 1995;21 (Part 1):621 were used.

Cell Culture and Preparation of Cell Membranes

CHO K1 cells expressing either human D2 and D4.2 receptors were grown in 162 $cm^2$ culture flasks in F12 medium (Gibco Laboratories, Grand Island, N.Y.) supplemented with 10% fetal bovine serum (FBS, Hyclone, Logan, Ut.) in an atmosphere of 5% $CO_2$/95% air at 37° C. Cells were grown until confluent after which growth medium was removed and replaced with 0.02% ethylene diamine tetraacetate (EDTA) in a phosphate-buffered saline solution (Sigma Chemical Co., St. Louis, Mo.) and scraped from the flasks. The cells were centrifuged at about 1000×g for 10 minutes at 4° C. and then resuspended in TEM buffer (25 mM Tris-HCL, pH 7.4, 5 mM EDTA, and 6 mM $MgCl_2$) for D2 or the D4.2 buffer (50 mM Tris-HCl, pH 7.4, 5 mM EDTA, 1.5 mM $CaCl_2$, 5 mM KCl, and 120 mM NaCl) and homogenized. The membranes were pelleted by centrifugation at 20000×g at 4° C. for 20 minutes. Then the pellets were resuspended in appropriate buffer at 1 mL/flask and stored at −70° C. until used in the receptor binding assay.

Receptor Binding Assays: D2, D4.2 Dopamine Receptors

A cell membrane preparation (400 μL) was incubated in triplicate with 50 μL [$^3$H]spiperone (0.2 nM for D2, 0.2 nM for D4.2), 50 μL buffer, or competing drugs where appropriate to give a final volume of 0.5 mL. After 60 minutes incubation at 25° C., the incubations were terminated by rapid filtration through Whatmann GF/B glass fibre filters (soaked for 1 hour in 0.5% polyethylenimine) on a cell harvester, with 3 washes of 1 mL ice-cold buffer. Individual filter disks containing the bound ligand were placed in counting vials with 4 mL of scintillation fluid (Ready Gel, Beckman Instrument, Inc., Fullerton, Calif.) and then counted in a Beckman LS-6800 liquid scintillation counter at an efficiency of 45%. Nonspecific binding was defined in presence of 1 mM of haloperidol.

Data Calculation

Saturation and competition binding data were analyzed using an iterative nonlinear least square curve-fitting Ligand program. In competition experiments, apparent $K_i$ values were calculated from $IC_{50}$ values by method of Cheng and Prusoff, "Relationship between the inhibition constant ($K_i$) and the concentration of inhibitor which causes 50% inhibition ($IC_{50}$) of an enzymatic reaction." *Biochem.*

*Pharmacol.*, 1973;22:3099–3108. Experimental compounds were made up as stock solutions in dimethyl sulfoxide (DMSO). The final concentration of 0.1% DMSO used in the incubation mixture had no effect on the specific binding. Each observation was carried out in triplicate. To allow these calculations, $K_d$ values were measured for the interaction of various ligands with the receptor. These were: [$^3$H]spiperone binding, human D2, 0.116+0.01 and human D4.2, 0.093+0.005 nM (n=3). The test results are presented below in Table 1 and Table 2.

TABLE 1

| Example No. | Dopamine Receptor Binding $K_i$ (nM) | |
|---|---|---|
| | $D_4$ | $D_2$ |
| 1q | 1334 | — |
| 2 | 0.2 | 268 |
| 2a | 4.4 | 1404 |
| 2b | 20.9 | 5116 |
| 2c | 11.9 | 2671 |
| 2d | 0.53 | 228 |
| 2e | 383 | — |
| 3 | 11.4 | 277 |
| 3b | 26.9 | 5729 |
| 3e | 5.6 | 1319 |
| 3f | 2.7 | 64.0 |
| 3g | 37.8 | — |
| 4 | 1.2 | 90.0 |
| 4a | 45.8 | — |
| 4b | 136 | — |
| 4c | 0.96 | 391 |
| 4d | 30.0 | — |
| 4e | 33.1 | — |
| 4f | 1.7 | 227 |
| 4g | 1.2 | 118 |
| 4h | 0.84 | 245 |
| 5 | 4.7 | 364 |
| 6a | 10.9 | 782 |
| 6b | 10.7 | 3213 |
| 6d | 103 | — |
| 6e | 74.9 | — |
| 9d | 5.4 | 1950 |
| 11 | 3.1 | 556 |
| 15 | >1000 | — |

TABLE 2

Additional Compounds

| Example No. | Dopamine Receptor Binding $K_i$ (nM) | |
|---|---|---|
| | $D_4$ | $D_2$ |
| 16g | 1.3 | 373 |
| 16h | 2.1 | 879 |
| 16i | 6.1 | 130 |

What is claimed is:

1. A method of treating psychosis or schizophrenia, the method comprising administering to a patient suffering therefrom a therapeutically effective amount of a compound having the Formula I

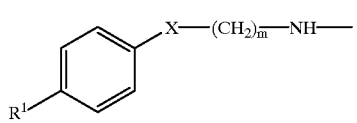

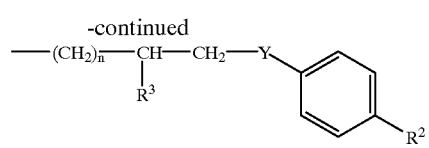

wherein
  $R^1$ and $R^2$ are independently hydrogen, hydroxy, $C_1$–$C_6$ alkyl, $C_1$–$C_6$ alkoxy, halogen, nitro, phenyl, cyano, carboxy, carboxyamido, carboxyalkyloxy, $C_1$–$C_6$ alkylamino, or $C_1$–$C_6$ dialkylamino;
  $R^3$ is hydrogen, hydroxy, or $C_1$–$C_6$ alkyl;
  X is $CH_2$, or $SO_2$;
  Y is O, $CH_2$, S, SO, or $SO_2$;
  m and n are independently 1–3;
  provided that X and Y are not both $CH_2$, further provided that one of $R^1$ and $R^2$ is not hydrogen, or the pharmaceutically acceptable salts thereof.

2. A method of treating psychosis or schizophrenia, the method comprising administering to a patient suffering therefrom a therapeutically effective amount of a compound having the Formula I

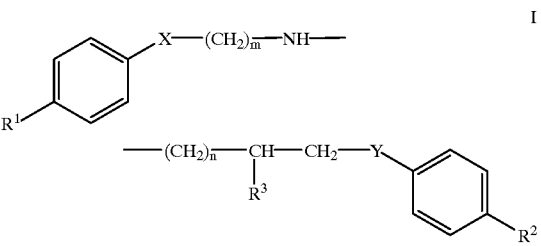

wherein
  $R^1$ and $R^2$ are independently hydrogen, hydroxy, $C_1$–$C_6$ alkyl, $C_1$–$C_6$ alkoxy, halogen, nitro, phenyl, cyano, carboxy, carboxyamido, carboxyalkyloxy, $C_1$–$C_6$ alkylamino, or $C_1$–$C_6$ dialkylamino;
  $R^3$ is hydroxy;
  X and Y are independently $CH_2$, O, S, SO, or $SO_2$;
  m and n are independently 1–3;
  provided that X and Y are not both $CH_2$, further provided that one of $R^1$ and $R^2$ is not hydrogen, or the pharmaceutically acceptable salts thereof.

3. The method of claim 1 wherein $R^3$ is —OH.
4. The method of claim 1 wherein $R^1$ is hydrogen.
5. The method of claim 2 wherein $R^1$ is hydrogen.
6. The method of claim 1 wherein $R^2$ is hydrogen.
7. The method of claim 2 wherein $R^2$ is hydrogen.
8. The method of claim 1 wherein X is $CH_2$ and Y is O.
9. The method of claim 2 wherein X is O and Y is $SO_2$.
10. The method of claim 2 wherein X is $CH_2$ or O, $R^3$ is OH, and Y is O.
11. The method of claim 2 wherein X is O and Y is O.
12. The method of claim 1 wherein X is $CH_2$ and Y is $SO_2$.
13. A method of treating psychosis or schizophrenia, the method comprising administering to a patient suffering therefrom a therapeutically effective amount of a compound selected from the group consisting of:
  (3-Phenoxy-propyl)-(3-phenyl-propyl)-amine hydrochloride;
  [3-(3-Methoxy-phenoxy)-propyl]-(3-phenyl-propyl)-amine hydrochloride;
  (3-Phenoxy-propyl)-(3-p-tolyl-propyl)-amine hydrochloride;

[2-(2-Ethoxy-phenoxy)-ethyl]-(4-phenyl-butyl)-amine hydrochloride;
[3-(3-Methoxy-phenoxy)-propyl]-(3-p-tolyl-propyl)-amine hydrochloride;
1-(3-Phenoxy-propylamino)-3-o-tolyloxy-propan-2-ol;
1-(2-Chloro-phenoxy)-3-(3-phenyl-propylamino)-propan-2-ol;
1-(2-Phenoxy-ethylamino)-3-m-tolyloxy-propan-2-ol;
1-[2-(3,4-Dichloro-phenyl)-ethylamino]-3-m-tolyloxy-propan-2-ol;
3-[3-(3-Phenyl-propylamino)-propoxy]-phenol hydrochloride;
(2-Benzenesulfonyl-ethyl)-[2-(2-ethoxy-phenoxy)-ethyl]-amine hydrochloride;
(3-Benzenesulfonyl-propyl)-[2-(2-ethoxy-phenoxy)-ethyl]-amine oxalate;
1-(3-Phenyl-propylamino)-3-o-tolyloxy-propan-2-ol;
1-(3-Phenyl-propylamino)-3-m-tolyloxy-propan-2-ol;
1-Phenoxy-3-(2-p-tolyloxy-ethylamino)-propan-2-ol; and,
1-[2-(4-Chloro-phenoxy)-ethylamino]-3-phenoxy-propan-2-ol.

* * * * *